United States Patent [19]

Nassi et al.

[11] Patent Number: 5,121,749
[45] Date of Patent: Jun. 16, 1992

[54] POSITION IN DEPENDENT VOLUMETRIC FLOW MEASURING APPARATUS

[75] Inventors: Menahem F. Nassi, Palo Alto; Jeffrey S. Frisbie; Stanley Levy, Jr., both of San Jose, all of Calif.

[73] Assignee: Cardiometrics, Inc., Mountain View, Calif.

[21] Appl. No.: 581,012

[22] Filed: Sep. 12, 1990

Related U.S. Application Data

[63] Continuation-in-part of Ser. No. 254,317, Oct. 5, 1988, Pat. No. 4,869,263.

[51] Int. Cl.⁵ .......................... A61B 8/12; A61B 5/02
[52] U.S. Cl. .................................. 128/692; 128/713; 128/662.06
[58] Field of Search ............... 128/713, 673, 662.06, 128/692; 604/96-103

[56] References Cited

U.S. PATENT DOCUMENTS

| | | | |
|---|---|---|---|
| 4,721,115 | 1/1988 | Owens | 128/713 |
| 4,869,263 | 9/1989 | Segal et al. | 128/662.06 |
| 4,947,852 | 8/1990 | Nassi et al. | 128/662.06 |

Primary Examiner—Francis Jaworski
Attorney, Agent, or Firm—Flehr, Hohbach, Test, Albritton & Herbert

[57] ABSTRACT

Apparatus for measuring the volumetric flow of a liquid in a vessel having a wall and having an axis extending longitudinally of the vessel parallel to the vessel wall. A flexible catheter is provided which has a longitudinal axis adapted to be disposed in the vessel. The catheter has front and back sides. First, second, third and fourth transducers are carried by the catheter. The first, second and fourth transducers are disposed on the front side of the catheter and the third transducer is positioned on the back side of the catheter. The second and fourth transducers are spaced apart a predetermined distance. The first, second and third transducers comprise a first set of transducers and the first, third and fourth transducers comprise a second set of transducers. Instrumentation is connected to the first, second, third and fourth transducers. The instrumentation causes the first, second, third and fourth transducers to emit ultrasonic energy beams therefrom. The first transducer is positioned on the catheter to emit an ultrasonic energy beam at an angle with respect to the longitudinal axis of the catheter. The second and third transducers are positioned in the catheter to emit ultrasonic beams extending generally perpendicular to the longitudinal axis of the catheter. The fourth transducer is positioned so that it emits an ultrasonic beam. The instrumentation receives the signals from the first, second, third and fourth transducers and measures the velocity of profile of the flow of liquid in the vessel by Doppler shift and ascertains the diameter of the vessel in the vicinity of the transducers. The instrumentation is capable of ascertaining which of said first and second sets of transducers provides more accurate velocity profile and diameter measurements of the vessel.

22 Claims, 4 Drawing Sheets

POSITION INDEPENDENT VOLUMETRIC FLOW MEASURING APPARATUS

This is a continuation-in-part of application Ser. No. 254,317 filed on Oct. 5, 1988 and now U.S. Pat. No. 4,869,263.

This invention relates to a volumetric flow measuring apparatus and catheter for use therein which is less position dependent and method.

In co-pending application Ser. No. 254,317 filed on Oct. 5, 1988, there is disclosed an apparatus and method for continuously measuring volumetric blood flow using multiple transducers. In that application there is disclosed positioning of such a multiple transducer catheter within a vessel such as the main pulmonary artery so as to obtain accurate volumetric flow measurements. During utilizing such a multiple transducer catheter and method, it has been found that certain doctors have had some difficulty in ascertaining the correct position for the catheter. In addition, it has been found that even after the catheter has been correctly positioned, after a period of time, as for example, in an intensive care unit, movement of the catheter may occur requiring repositioning of the catheter. Since typically attendant nurses are not permitted to reposition the catheter, there is still a need for obtaining accurate volumetric readings until a physician can be summoned. Also, there is a need for a catheter to provide accurate volumetric readings for substantial periods of time without the need for repositioning.

Also, in application Ser. No. 254,317 filed on Oct. 5, 1988, there is disclosed an apparatus and method for continuously measuring volumetric blood flow which utilizes a catheter having predetermined bends at the distal extremity thereof and in which a positioning device is used to alter the shape of the bends prior to insertion of the catheter into the patient. The positioning device is extended to enlarge the angle of the predetermined bend to enable the tip of the catheter to negotiate with an inflated balloon the right atrium, the right ventricle and to the main pulmonary artery and finally out to the right branch of the pulmonary artery. Thereafter, the positioning device is typically retracted and thereafter acts as a passive element providing some support to the catheter but not in the region of the predetermined bend. It has been found that it is desirable to eliminate the complexity of the catheter to make it easier for the cardiovascular surgeon to utilize it in cardiovascular procedures. There is therefore a need for a volumetric flow measuring apparatus and method which is less position dependent.

In general, it is an object of the present invention to provide a volumetric flow measuring apparatus and method which is less position dependent.

Another object of the invention is to provide an apparatus and method of the above character in which redundancy is provided by providing one or more additional transducers.

Another object of the invention is to provide an apparatus and method of the above character which substantially reduces the need for repositioning of the catheter.

Another object of the invention is to provide a method and apparatus of the above character in which a catheter is utilized which eliminate the need for a movable guide wire.

Another object of the present invention is to provide a catheter which utilizes an elongate wire in a fixed position which is used to stiffen certain portions of the catheter.

Another object of the invention is to provide an apparatus and method of the above character in which real time feedback is provided to aid in the positioning of the catheter.

Another object of the invention is to provide an apparatus and method of the above character in which error criteria are defined such that gradual signal degradation or improvement is displayed continuously to aid in placement of the catheter by the physician and at the same time optimizing a displayed figure of merit for the received signals.

Another object of the invention is to provide an apparatus and method of the above character in which the optimum transducer configuration is selected.

Another object of the invention is to provide an apparatus and method of the above character in which real time flow measurements are displayed.

Additional objects and features of the invention will appear from the following description in which the preferred embodiment is set forth in detail in conjunction with the accompanying drawings.

In general, the apparatus is for measuring volumetric flow of liquid in a vessel which has a wall and an axis extending longitudinally of the vessel parallel to the vessel wall. A flexible catheter which has a longitudinal axis is provided and is adapted to be disposed in the vessel. First, second and third ultrasonic transducers are carried by the catheter on one side of the catheter and are spaced apart longitudinally of the catheter. The second and third transducers are spaced apart a predetermined distance. The first and second transducers comprise one set of transducers and the first and third transducers comprising another set of transducers. Instrumentation means is provided which is connected to the first, second and third transducers for causing them to emit ultrasonic energy beams therefrom. The first of the ultrasonic transducers is positioned on the catheter to emit an ultrasonic energy beam at an angle with respect to the longitudinal axis of the catheter and the second and third transducers are positioned on the catheter to emit ultrasonic beams extending generally perpendicular to the longitudinal axis of the catheter. The instrumentation means provided includes means connecting the first, second and third transducers whereby the first transducer measures the velocity profile of the flow of the liquid in the vessel by Doppler shift measurements and the second and third transducers are used for measuring the velocity profile of the flow of the liquid in the vessel by Doppler shift measurements and at least a portion of the diameter of the vessel at the location that the transducer is positioned on the catheter. The instrumentation means also includes means for ascertaining which of the first and second sets, or all, of ultrasonic transducers provides the optimal velocity profile and diameter measurements. The instrumentation means also includes means for sensing an error condition when an optimal measurement is not available from the catheter as it is positioned.

Figures 1, 2:
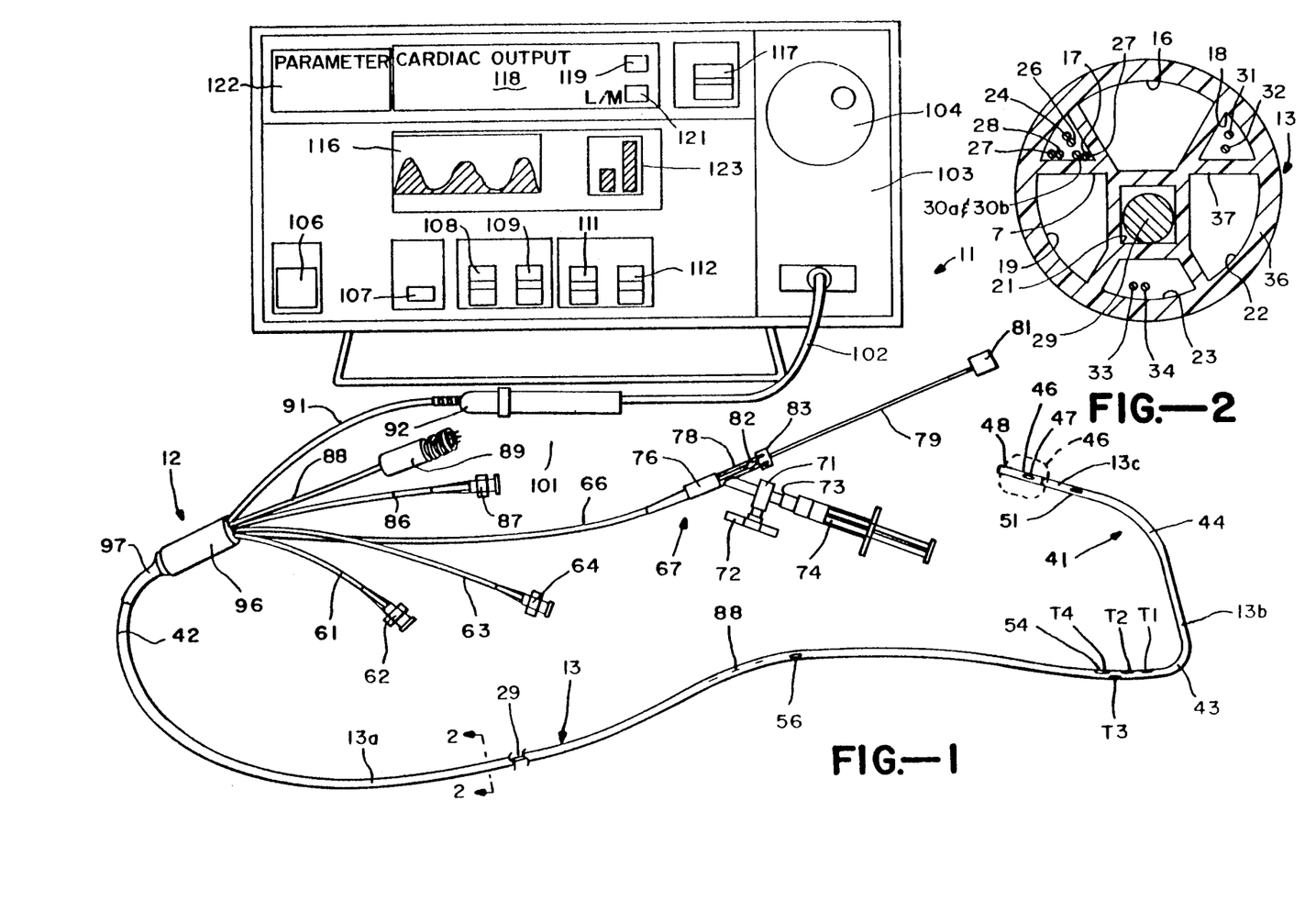
FIG. 1 is an isometric view of an apparatus for continuously measuring volumetric blood flow incorporating the present invention.
FIG. 2 is a cross sectional view taken along the line 2—2 of FIG. 1.

More specifically, the apparatus and method for continuously measuring volumetric blood flow using multiple transducers is shown in FIG. 1. As shown therein the apparatus consists of a control console 11 and a catheter 12 which is connected to the control console 11. The catheter 12 consists of a flexible elongate member 13 formed of suitable material such as plastic. A cross-sectional view of the elongate member 13 is shown in FIG. 2 and as shown therein, the flexible elongate member 13 is provided with a plurality of lumens 16, 17, 18, 19, 21, 22 and 23 for a total of 7 lumens. As shown, the lumens are of various sizes and perform different functions. For example, lumen 16 is utilized for providing pressure monitoring, also serves as a possible injectate lumen and it accommodates the front distal, intermediate and proximal transducers T4, T2 and T1. Lumen 17 is provided for the wires 24, 26, 27, 28 and 30a and 30b for the front proximal, intermediate and distal transducers T4, T2 and T1 respectively. Lumen 18 is provided for the thermistor and the thermistor wires 31 and 32. Lumen 19 is utilized for providing pressure monitoring and serves as a possible injectate lumen. Lumen 21 is provided for a guide wire 29 and also serves as a balloon inflation and deflation lumen. Lumen 22 is used to provide pressure monitoring and also serves as a possible injectate lumen. Lumen 22 generally indicates right ventricular or main pulmonary artery pressure. Lumen 23 accommodates the wires 33 and 34 for the back transducer T3.

In the preferred embodiment, lumen 16 provides right arterial pressure monitoring and serves as an injectate lumen. Lumen 19 provides distal or pulmonary wedge pressure monitoring. Lumen 22 provides pressure monitoring in the area of the transducers, so as to indicate their position and serves as an injectate lumen.

It has been found that these seven lumens can be provided in flexible plastic tubing 13 having an outside diameter of 0.098 inches plus or minus 0.003 inches. The outside circular wall 36 has a minimum thickness of approximately 0.007 inches. The septa 37 dividing the lumens should have minimum thicknesses of approximately 0.004 inches.

As can be seen from FIG. 1, the distal extremity or tip 41 of the elongate member 13 is generally U-shaped. The flexible elongate member 13 is provided with a substantially straight flexible portion 13a having a length of approximately 110 centimeters. The U-shaped tip 41 configuration has a length of approximately 15 centimeters for a total length of 125 centimeters for the elongate member 13. The flexible elongate member 13 is provided with another relatively straight portion 13b extending beyond an approximately 90° bend 43. It also is provided with another generally straight portion 13c extending beyond a more gently curved approximately 60° bend 44.

An inflatable flotation balloon 46 is mounted on the distal extremity of the portion 13c by suitable means such as an adhesive. The balloon is formed of a suitable material such as latex and can be inflated and deflated by a fluid passing through an inflation and deflation port 47 which is in communication with the balloon inflation lumen 21. The balloon 46 will take a generally spherical configuration as shown in dotted lines when inflated and can be inflated to a suitable diameter as, for example, 10 to 14 millimeters. As can be seen the portion 13c extends through the balloon and is provided with a distal pressure port 48 which is in communication with the lumen 19.

A thermistor 51 of a conventional construction is mounted in the portion 13c proximal of the balloon 46 intermediate of the bend 44 and the balloon 46. It is mounted in the space occupied by the lumen 18. The thermistor 51 is connected to conductors 31 and 32 which extend through the lumen 18.

Additional ports are provided in the catheter 12 and include a positioning port 54 which is in communication with the lumen 22 and a right atrial pressure port and injectate port 56 which is in communication with the lumen 16. Both of the ports 54 and 56 are located near the distal extremity of the flexible elongate member 13 with the port 54 being located from 1 to 3 centimeters from the proximal end of the bend 43 and the port 56 being located approximately 18 centimeters from the port 54.

The proximal extremity of the elongate member 13 is connected to a plurality of fittings through a manifold molding 96 as shown in FIG. 1. Thus there is provided an elongate flexible member 61 which is provided with a Luer-type fitting 62. The flexible elongate tubular member 61 is connected to the right atrial pressure lumen 16. Another elongate flexible tubular member 63 is provided with a Luer-type fitting 64 and is connected to the distal pressure lumen 19. Another flexible elongate member 66 is connected to the balloon inflation lumen 21. A two arm adapter 67 is mounted on the tubular member 66 that is connected to a stop cock 71 which is provided with a handle 72 and a Luer-type fitting 73. A syringe 74 of a conventional type is provided which carries a fluid of a suitable type such as carbon dioxide which can be used for inflating and deflating the balloon 46. The adapter 67 is also provided with a central arm 76.

The guide wire 29 serves as a positioning and straightening device and extends through the lumen 21 and has a suitable diameter such as 0.012 inches. The guide wire 29 is formed of a suitable material such as stainless steel and is attached to a relatively straight piece of hypodermic tube 79 having a suitable diameter such as 0.042 inches and is also formed of a suitable material such as stainless steel. The tube 79 has a length such that it extends approximately the entire length of the flexible elongate member 66. A knob 81 is secured to the proximal extremity of the tube 79 and is used for advancing and retracting the guide wire 29. The guide wire 29 has a length so that when the knob is pushed forward into the central arm 76, the guide wire 29 extends through to the distal extremity or tip 41 of the catheter 12 to substantially straighten the same to facilitate insertion of the catheter 12 into the vessel of the human body and also to facilitate advancement of the same as the inflated balloon 46 is utilized to advance the catheter as hereinafter described. A raised section such as solder joint or other means 82 on the tube 79 serves as a stop to prevent retraction of the tube 79 through a removable cap 83 carried by the central arm 76. The proximal extremity of the wire 29 and the tube 79 are joined together by conventional means such as solder or by crimping.

Another flexible elongate element 86 with a Luer-type fitting 87 is provided which is in communication with the positioning pressure lumen 22. Another flexible elongate tubular member 88 is in communication with the lumen 18. It is provided with a thermodilution connector 89 of a conventional type. Another flexible elongate member 91 is provided which has wires extending therethrough which are connected to the back transducer provided in the lumen 23 and the front transducer wires provided in lumen 17. The elongate member 91 is connected to a connector 92 which is connected to all of the wires extending through the elongate member 91. A manifold molding 96 is provided around the proximal extremity of the flexible elongate member 13 and the distal extremities of the flexible elongate members 61, 63, 66, 86, 88 and 91. A strain relief and reinforcing member 97 formed of a suitable material such as rubber extends out of the molding 96 and covers the proximal extremity 42 of the flexible elongate element 13.

The connector 92 plugs into its corresponding connector 101 which is at the end of cable 102 that extends into the front panel 103 of the control console 11. As shown in FIG. 1, the control console includes a knob 104 provided on the front panel 103 which can be utilized for setting the alarm settings of the cardiac output limits and the diameter limits of the apparatus. A "power on" push button 106 is provided as well as an alarm muting push button 107. In addition, push buttons 108 and 109 can be provided for setting "alarm on", and "high" and "low" alarm limits for the cardiac output. Similarly, push buttons 111 and 112 can be provided for setting "alarm on", and "low" and "high" alarm limits for the diameter measurement. A graphic display 116 is provided for displaying instantaneous flow waveforms, flow trends or velocity profiles. Mode push buttons 117 are provided for selecting either a "monitor" or "insert" mode. A digital readout 118 is provided for displaying the cardiac output in liters per minute with push buttons 119 and 121 giving the capabilities to provide the mean cardiac and the peak cardiac outputs. In addition, a digital display 122 is provided for giving a readout of measured parameters such as the diameter of the vessel being monitored in millimeters, stroke volume or a cardiac index. Vertical LCD bars display 123 is provided adjacent the display 116. The bars display 123 by their heights give an indication of the validity of the acoustic information being processed by the control console 11 and thereby give an indication of the efficacy of position of the catheter in making correct velocity and volumetric flow measurements in the vessel in which it is positioned.

In accordance with the present invention, to obtain the type of information which is provided by the console 11, at least four ultrasonic transducers are carried by the catheter 12. Front and back transducers are provided as hereinafter described. The front transducers typically are mounted within the recess provided by the lumen 16 whereas the back transducers are provided in the lumen 23 which is diametrically opposite the lumen 16. The distal extremity bends 43 and 44 are formed within the plane which includes the longitudinal axis of the catheter 12 and a line passing diametrically through the catheter and through the middle of the front and back transducer lumens 16 and 23 respectively. This is necessary to orient the transducer beams such that each lies substantially within a single plane which includes the longitudinal axis of the main pulmonary artery when the catheter's distal extremity 13c is positioned downstream in one of the smaller branches of the right pulmonary artery. This beam positioning is essential to obtain accurate diameter and velocity profile measurements for calculating volumetric blood flow or cardiac output.

Figure 4A:
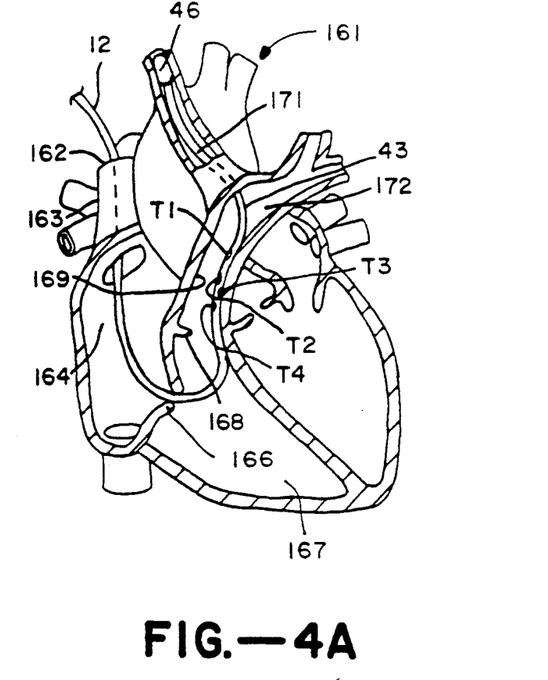
FIGS. 4A, 4B and 4C are cross sectional views of a human heart showing three different positions of the catheter of the present invention in the pulmonary artery of the heart.
Figure 4B:
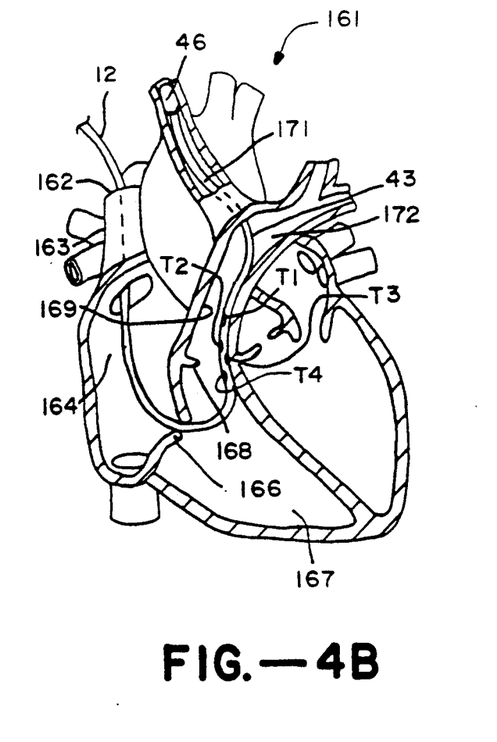
Figure 4C:
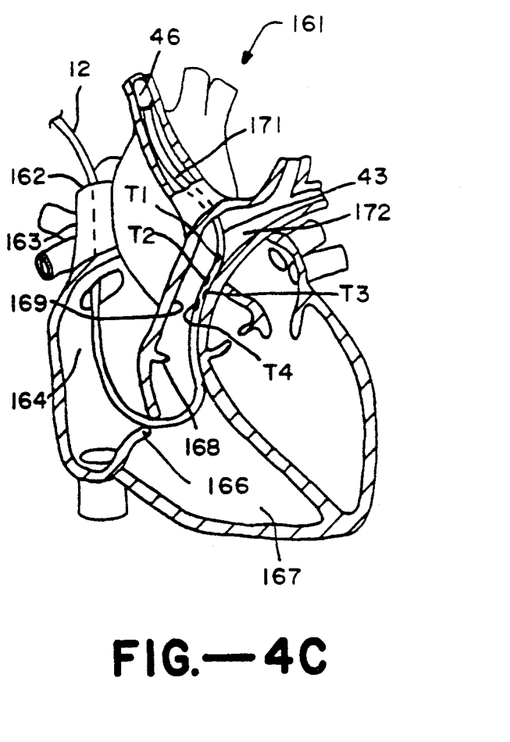

In FIGS. 4A, 4B and 4C, the catheter 12 is shown positioned within a human heart. The introduction of the catheter 12 through the jugular vein of the patient is a technique which is generally well known to those skilled in the art. In order to facilitate introduction, the guide wire 29 is advanced to its extreme distal position by operation of the knob 81 to straighten the distal extremity or tip 41 of the catheter 12 to facilitate introduction of the catheter into the jugular vein of the patient. The catheter 12 as shown in FIGS. 4A, 4B and 4C passes into the heart 161 through the venous port 162 of the superior vena cavae 163, through the right atrium 164, and then through the tricuspid valve 166, the right ventricle 167, through the pulmonary valve 168, through the main pulmonary artery 169 and into the right pulmonary artery branch 171 and then wedging downstream in one of the secondary branches leading from the right pulmonary artery branch with the tip of the catheter having the balloon thereon being disposed in that branch. In the course of inserting the catheter, its location can be monitored by observing the pressure waveforms which are quite distinct from one another in the different parts of the circulatory system. Adequate velocity and diameter determinations can generally be made with the transducers positioned in the region between pulmonic valve 168 and below bifurcation 172.

Figure 3:
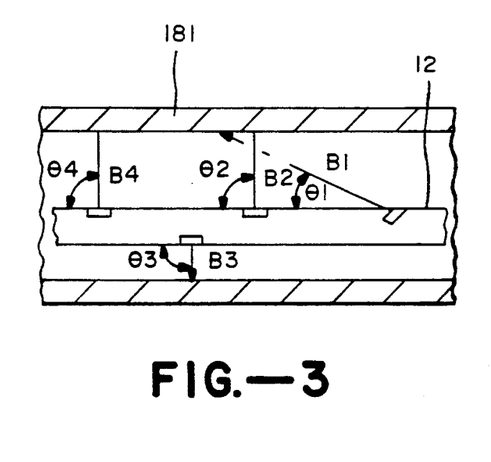
FIG. 3 is a schematic illustration of a catheter of the present invention disposed within a vessel for obtaining a volumetric flow rate utilizing four transducers on the catheter.

In the arrangement shown in FIGS. 1 and 3, it can be seen that first, second and fourth ultrasonic transducers T1, T2 and T4 are carried by the catheter on the front side of the catheter and are spaced longitudinally of the catheter 12. The second and fourth transducers or, in other words, the transducers T2 and T4 are spaced apart a predetermined distance. A third transducer T3 is provided on the back side of the catheter 12 opposite the transducers T1, T2 and T4 and faces in a direction which is 180° opposed to the direction in which the transducers T2 and T4 face. The transducer T3 may not be necessary when the catheter is immediately adjacent a wall of the vessel. As hereinafter described, the first and second transducers, transducers T1 and T2 serve as one set of transducers in conjunction with the third transducer T3 and the first and fourth transducers T1 and T4 form another set of transducers in conjunction with the third transducer T3. The control console 11 serves to supply electrical signals to the transducers through the connecting wires hereinbefore described to cause the transducers to emit ultrasonic energy beams as indicated by the rays B1, B2, B3 and B4 shown in FIG. 3. The first ultrasonic transducer T1 is positioned on the catheter so that it emits an ultrasonic energy beam B1 which is at an angle $\Theta 1$ with respect to the longitudinal axis of the catheter 12. The transducers T2, T3 and T4 emit ultrasonic beams B2, B3 and B4 at angles $\Theta 2$, $\Theta 3$ and $\Theta 4$ which are generally perpendicular to the longitudinal axis of the catheter 12. The beams B2, B3 and B4 are directed at angles which are substantially 90° with respect to the longitudinal axis of the catheter 12. The beam B3 is directed in a direction which is 180° or opposite to that of the beams B2 and B4.

In conjunction with the instrumentation means provided by the control console 11, the first transducer T1 measures the velocity profile of the liquid in the vessel 181 by Doppler shift measurements. The second and fourth transducers T2 and T4 are also used for measuring the velocity profile of the flow of the liquid in the vessel by Doppler shift measurements and at least a portion of the diameter of the vessel at the location that the transducer is positioned on the catheter. The third transducer T3 measures at least a portion of the diameter of the vessel at the location that the transducer is positioned on the catheter. The instrumentation means provided by the control console 11 also includes means for ascertaining which of the first and second sets, or all, of ultrasonic transducers provides optimal velocity profile and diameter measurements.

In the position of the catheter 12, shown in FIG. 4A, the catheter 12 either because of the vasculature of the heart or the longitudinal position of the catheter in the pulmonary artery or vessel in the heart has both of the transducers T2 and T4 on the front side of the catheter in good positions to receive the desired information to provide accurate velocity and volumetric blood flow through the vessel. The transducers T2 and T4 are both in optimum positions within the pulmonary artery to make accurate measurements. In this situation, instrumentation 11 will use either transducers T1, T2, and T3 as a set, or transducers T1, T4, and T3 as a set. Or, it may use all four transducers T1, T2, T3, and T4 as a set.

In the position of the catheter 12, as shown in FIG. 4B, there is depicted a situation in which the pulmonary artery is too short in comparison to the spacing between the catheter transducers T2 and T4 or the catheter 12 is somewhat proximal to the position where it should be located because the transducer T4 is in a region of or below the pulmonic valve 168 in the heart. For that reason the information supplied by the transducer T4 is inaccurate or inappropriate. However, the transducer T2 is still in a good position and therefore the instrumentation 11 will ascertain that this information is appropriate information and will supply the appropriate measurements utilizing transducers T1, T2 and T3 as the set of transducers, rather than the transducers T1, T4 and T3 as the set of transducers.

In FIG. 4C there is depicted a situation in which the transducer T2 may not provide good information with the situation being that the catheter 12 has been pushed too far distally or the pulmonary artery is quite long in comparison to the spacing between the transducers T2 and T4. In such a situation the instrumentation 11 will select the transducers T1, T3 and T4 as being the transducers to be utilized rather than the transducers T1, T2 and T3. The diameter transducers are used two at a time to measure diameter when the catheter 12 is not immediately adjacent a wall of the vessel. Thus, either T2 and T3 or T3 and T4 are used to measure the diameter of the vessel.

If the catheter 12 is positioned in such a manner that neither of the transducers T2 and T4 in conjunction with transducers T1 and T3 can provide good signals to provide accurate velocity profile and volumetric flow measurements, this situation is sensed by the instrumentation or control console 11, and an error signal will be provided on the control console 11 which will appear on the digital display. However, it can be seen that an error signal will only be generated by the control console 11 when neither the transducers T2 and T4 in conjunction with transducers T1 and T3 will provide a good measurement. Because of this factor, the position of the catheter 12 is much less position dependent and thus will give a range of accurate readings in a wider range along the longitudinal axis of the catheter 12 than would be possible with a single transducer such as transducer T2 or transducer T4.

Figure 5A:
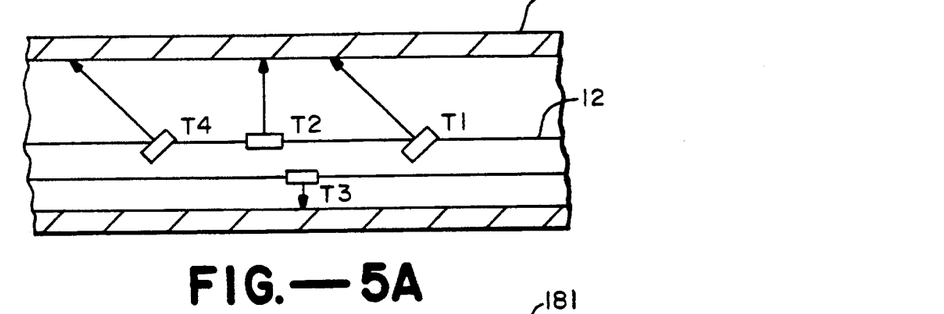
FIGS. 5A, 5B, 5C and 5D are schematic illustrations of various transducer arrangements on a catheter of the present invention.

It should be appreciated that if desired the fourth transducer T4 rather than being a diameter transducer can be positioned at an angle similar to transducer T1 to be a velocity transducer (see FIG. 5A). This would make it possible to select either of the velocity transducers T1 or T4 using always the two diameter transducers T2 and T3.

Figure 5B:
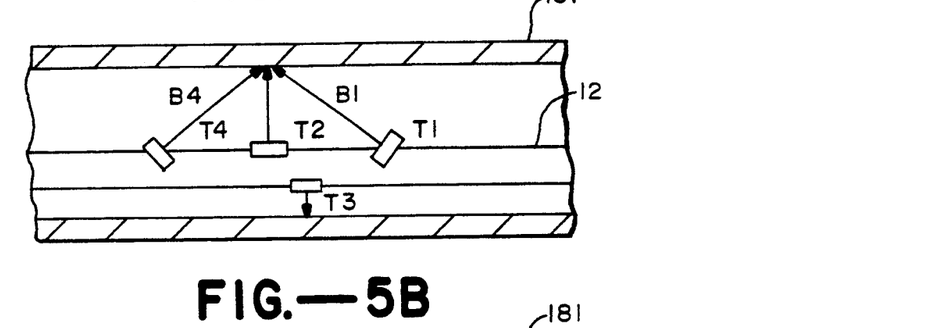

It should also be appreciated that if the fourth transducer T4 rather than being primarily a diameter transducer is instead a velocity transducer similar to T1, its beam direction can be opposite to that of T1. That is if beam B1 points upstream, beam B4 would point downstream, as in FIG. 5B.

Figure 5C:
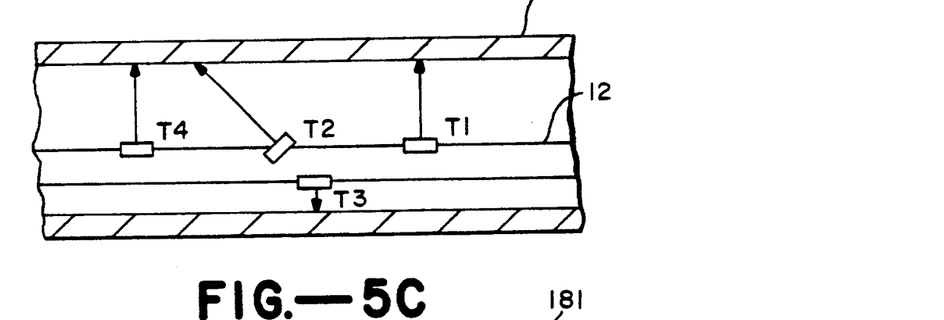
Figure 5D:
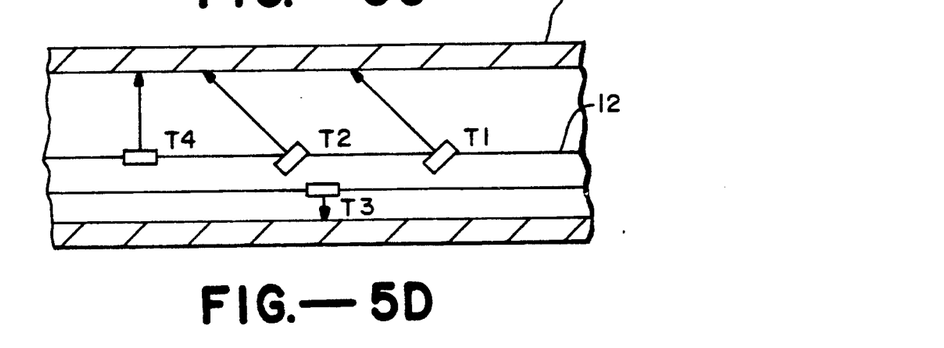

It should also be appreciated that transducers T1, T2, T3 and T4 can be in other orders and directions, depending on the algorithms used to analyze the velocity and diameter information and perform the flow calculations. As examples, T1, T3 and T4 could be primarily for diameters measurements, with T2 being used for velocity measurements (see FIG. 5C). Or, T3 and T4 could be used primarily for diameter measurements with T1 and T2 being for velocity measurements (See FIG. 5D).

In the past, a pressure port has been located adjacent to the transducers and this pressure port has been utilized as a key for positioning the catheter. However, with respect to the present catheter, this pressure port is merely used as a reference point when the positioning of the catheter has been accomplished more effectively by utilizing error criteria to determine the proper position of the catheter. This can be readily accomplished by utilizing error criteria in an algorithm incorporated into software implemented within the control console 11 to establish whether or not the diameter and the velocity signals being received are in fact accurate measurements. Appropriate data would be incorporated into the algorithm by channeling the algorithm. By channeling the algorithm data parallel with the signals being received from the transducer, the control console 11 can be utilized to detect errors in the input signals. Utilizing such information, appropriate instructions can be provided on the control console 11 to facilitate positioning of the catheter 12 in the vessel. For example, instructions can be given to advance or retract the catheter to improve the signals being received.

From the foregoing, be seen that there has been provided a volumetric flow measuring apparatus and method which is less position dependent. Because of the use of an additional transducer or transducers, the need for repositioning of the catheter is substantially reduced. Real time feedback is provided to aid in positioning of the catheter. Error criteria are defined such that gradual signal degradation or improvement is displayed continuously to aid in placement of the catheter by the physician while at the same time optimizing a displayed figure of merit for the received signals from the transducers.

Figures 6, 7:
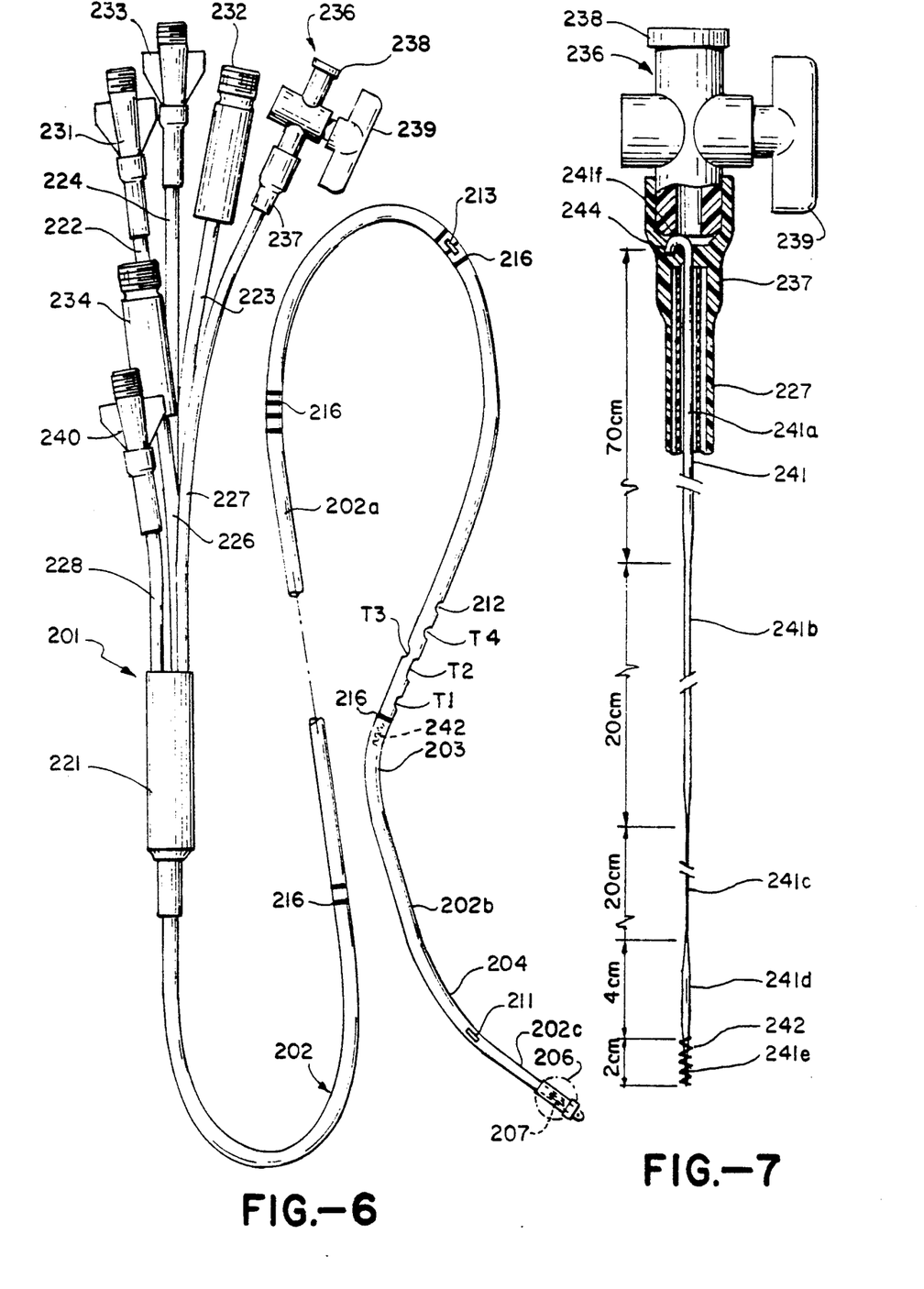
FIG. 6 is a plan view of an alternative embodiment of an ultrasonic pulmonary artery catheter which incorporates the present invention and eliminates the need for a movable guide wire.
FIG. 7 is an enlarged detail view of the fixed wire used in the catheter shown in FIG. 6.

It also has been found that in order to make the volumetric flow measuring apparatus and method less dependent upon positioning of the catheter that it is desirable to provide a catheter which does not utilize a movable guidewire. Such a catheter 201 is shown in FIGS. 6 and 7. The catheter 201 shown therein is adapted to be substituted for the catheter 12 and is adapted to be connected to the control console 11 shown in FIG. 1. This catheter 201 in many respects is very similar to the catheter 12 shown in FIG. 1 with the exception that the guidewire 79 utilized in the catheter assembly shown in FIG. 1 is eliminated. Also a gentle substantially J-shaped bend is provided in the distal extremity of the catheter 201 rather than the generally U-shaped bend provided in FIG. 1.

The catheter 201 shown in FIG. 6 consists of a flexible elongate member 202 formed of plastic. A cross section like FIG. 2 taken of the flexible elongate member in the position shown in FIG. 1 would provide a similar cross section in which a total of seven lumens are provided in the flexible elongate member 202.

The flexible elongate member 202 is provided with a relatively straight flexible portion 202a having a suitable length as for example approximately 110 cm up to a bend 203 of approximately 15° to 20° after which there is provided another flexible relatively straight portion 202b up to a bend 204 of another small angle as for example 15° to 20° after which there is provided another flexible relatively straight portion 202c extending to the distal extremity of the catheter 201. Thus, the bend 203 forms an angle of approximately 165° to 160° and bend 204 forms an angle of approximately 165° to 160°. Thus it can be seen that the bend 203 and 204 in the distal extremity of the catheter 201 provide a very gentle curvature which represents a substantially modified J-bend. An inflatable latex balloon 206 is provided on the distal extremity of the flexible elongate member 202 and is adapted to be inflated and deflated through a port 207.

A thermistor 211 is mounted in the portion 202c adjacent the bend 204. Transistors T1, T2, and T4 are mounted on the front side of the flexible elongate member 202 proximal of the bend 203 and the transistor T3 is provided on the backside of the member 202 opposite and between the transducers T2 and T4. However, it should be appreciated that the four transducers can be arranged in any of the manners heretofore described. A main pulmonary artery port 212 is provided in the flexible elongate member 202 slightly proximal of the transistor T4 and a right atrial port 213 is provided proximal of the port 212.

Markers 216 visible to the human eye of a conventional type are provided on the exterior surface of the flexible elongate member 202 and are spaced longitudinally thereof. The markers 216 serve to indicate to the surgeon how far the catheter 201 has been introduced into the patient.

The proximal extremity of the flexible elongate member 202 is connected through a manifold 221 to a plurality of flexible elongate members 222, 223, 224, 226, 227 and 228. The flexible elongate member 222 is connected to the distal pressure lumen and is provided with a Luer adapter 231 at its proximal extremity. The flexible elongate member 223 carries the conductors provided in the flexible elongate member 202 connected to the devices in the catheter. The conductors in the elongate member 223 are connected to an electrical connector 232 at the proximal extremity of the flexible elongate member 223.

The flexible elongate member 224 is provided with a Luer adapter 233 at its proximal extremity. The flexible elongate member 226 is provided with an electrical connector 234 adapted to be connected to a conventional thermodilution console (not shown). The flexible elongate member 227 is connected to the balloon inflation lumen and is provided with a stop cock 236 which is secured to the flexible elongate member 227 with an adapter 237. The stop cock 236 is provided with a Luer type fitting 238 and a handle 239. The flexible elongate member 228 is connected to the right atrial pressure lumen and is provided with a Luer adapter 240.

Suitable means is provided for giving additional stiffness to the flexible elongate member 202 which is just short of the pre-formed bend 203 to provide support and additional rigidity to the catheter throughout substantially its entire length except in the region of the pre-formed bend 203 and beyond to the distal extremity of the catheter. The predetermined bends 203 and 204 have been provided in the flexible elongate member 202 to provide stability for the catheter 201 when the catheter 201 is positioned in the pulmonary artery. One means for providing this additional rigidity and stiffness in the flexible elongate member 202 is obtained by utilizing a flexible elongate element 241 in the form of a wire of a suitable material such as stainless steel. The wire 241 has a length so that it extends substantially the entire length of the flexible elongate member 202. Its proximal extremity 241a has a suitable diameter such as 0.014" which diameter continues for a suitable distance as for example 70 cm. The wire 241 is ten taper ground to a diameter of 0.012" to provide a portion 241b that extends for approximately 20 additional centimeters. Another tape grind then reduces the diameter of the wire 241 to 0.009" to provide a portion 241c which extends for approximately another 20 centimeters to a region adjacent the transducers a portion 241d is provided on the wire 241 which has a larger diameter of 0.014" for a distance of 2 to 3 centimeters. The wire portion 241d serves to provide increased stiffness in the region of the catheter 201. The distal extremity of the wire 241 is provided with a portion 241e which has a continuous taper in which the diameter of the wire is reduced from 0.014" to 0.0025" to give additional flexibility to the distal extremity of the wire 241. A coil spring 242 is mounted on the wire 241 by having the tapered portion 241e extend into the coil 242 and be secured thereto by suitable means such as solder. The spring 242 is formed of a suitable material such as 0.002" diameter stainless steel wire. The spring has a suitable outside diameter as for example 0.014" and a length of approximately 2 cm. The wire 241 with the spring 242 is positioned so that spring 242 is just short of the bend 203. This makes it possible for the distal extremity of the catheter 11 to have good flexibility so that it can be floated into the desired position upon inflation of the balloon 206. At the same time, wire 241 provides additional rigidity to the catheter 201 to facilitate its insertion into the vessel of the patient.

The proximate extremity of the wire 241 is provided with a right angle hook portion 241f which is positioned in a hole 244 in the adapter 237 and is retained therein by the stopcock 236 (see FIG. 7).

The use of the catheter 201 in the volumetric flow measuring apparatus shown in FIG. 1 is very similar to that hereinbefore described in conjunction with the apparatus shown in FIG. 1. However, it has been found that the catheter 201 makes the catheter less position dependent because the elimination of the movable wire removes another variable in the positioning of the catheter in a desired position within the heart of the patient. This is true because after removal of the movable wire from the distal extremity of the catheter, the distal extremity of the catheter has a different flexibility than when the guidewire was positioned in the distal extremity making it more difficult for the instrumentation 11 to ascertain whether or not the catheter 12 has been properly positioned in the heart. With the use of the fixed wire which only extends up to the bend 203, the flexibility of the distal extremity of the catheter 201 remains constant. The fixed wire 241 provides additional rigidity throughout the remainder of the catheter while providing the desired transitions in flexibility in the regions leading up to the portions of the catheter carrying the transducers T1, T2, T3 and T4 while still providing the desired rigidity within the catheter at that region. The spring 242 provides graduated transition at the distal extremity of the wire 241 and provides a relatively blunt end so that the wire 241 will not puncture the flexible elongate element 202. Alternatively if desired the spring 242 can be eliminated and a blunt end can be formed on the end of the wire 241 for a similar purpose.

The relatively small angle preformed bends 203 and 204 provided in the distal extremity of the catheter 201 make it possible for the catheter 201 to negotiate the vessels of the patient and make it possible to facilitate positioning the distal extremity of the catheter in the appropriate position in the heart to thereby properly position the transducers T1 through T4. The bends 203 and 204 also provide the necessary stability for the distal extremity of the catheter during the time that measurements are being made by the instrumentation console 11 from information supplied by the transducers T1 through T4.

From the foregoing it can be seen that the catheter which is shown in FIGS. 6 and 7 can be utilized in the volumetric flow measuring apparatus and method heretofore described to provide a less position dependent apparatus and method. The elimination of the movable wire eliminates one additional variable from the system. This makes it possible to more accurately predict when the catheter has been properly positioned in the heart to make accurate volumetric flow measurements.

What is claimed is:

1. In an apparatus for measuring the volumetric flow of a liquid in a vessel having a wall and having an axis extending longitudinally of the vessel parallel to the vessel wall, a flexible catheter having an longitudinal axis adapted to be disposed in the vessel, said catheter having front and back sides, first, second, third and fourth transducers carried by the catheter, said first, second and fourth transducers being disposed on the front side of the catheter and the third transducer being positioned on the back side of the catheter, said second and fourth transducers being spaced apart a predetermined distance, the first, second and third transducers comprising a first set of transducers and the first, third and fourth transducers comprising a second set of transducers, instrumentation means connected to the first, second, third and fourth transducers, said instrumentation means including means for causing the first, second, third and fourth transducers to emit ultrasonic energy beams therefrom, the first transducer being positioned on the catheter to emit an ultrasonic energy beam at an angle with respect to the longitudinal axis of the catheter, the second and third transducers being positioned in the catheter to emit ultrasonic beams extending generally perpendicular to the longitudinal axis of the catheter, the fourth transducer being positioned so that it emits an ultrasonic beam, said instrumentation means includes means for receiving the signals from the first, second, third and fourth transducers and for measuring the velocity of profile of the flow of liquid in the vessel by Doppler shift and for ascertaining the diameter of the vessel in the vicinity of the transducers, said instrumentation means including means for ascertaining which of said first and second sets of transducers provides more accurate velocity profile and diameter measurements of the vessel.

2. Apparatus as in claim 1 wherein said instrumentation means includes means for ascertaining which set of transducers provides an optimal measurement.

3. Apparatus as in claim 1 wherein said instrumentation means includes means for generating an error signal when accurate velocity and diameter measurements cannot be ascertained from either of the first and second sets of transducers.

4. Apparatus as in claim 1 wherein said instrumentation means includes means for periodically sampling the output from the first and second sets of transducers and for switching from one set of transducers to another set of transducers in the event the measurements from one set of transducers is better than the measurements from the other set of transducers.

5. Apparatus as in claim 1 wherein the fourth transducer is positioned so that it measures the diameter of the vessel.

6. Apparatus as in claim 1 wherein said fourth transducer is positioned so that the beam therefrom extends at an angle with respect to the longitudinal axis so as to be capable of measuring velocity of the flow of liquid in the vessel.

7. Apparatus as in claim 1 wherein a catheter has a distal extremity and wherein first and second bends are provided in the distal extremity and wherein the first, second, third and fourth transducers are positioned in the proximity to the first bend of the catheter.

8. Apparatus as in claim 7 wherein said catheter is provided with a supplemental stiffening means for providing additional graduated stiffening to the catheter from the proximal extremity of the catheter to a portion which just extends beyond the first, second, third and fourth transducers positioned in the catheter.

9. Apparatus as in claim 8 wherein said graduated stiffening means includes means which provides increased stiffness in the catheter in the vicinity of the first, second, third and fourth transducers to compensate for openings provided in the catheter to accommodate the transducers.

10. Apparatus as in claim 8 wherein said supplemental stiffening means is in the form of a wire extending through the catheter.

11. Apparatus as in claim 10 wherein the wire is provided with a distal extremity together with spring means secured to the distal extremity of the wire.

12. In a method for measuring the volumetric flow of a liquid in a vessel which has a wall and an axis extending longitudinally of the vessel parallel to the vessel wall by the use of a flexible catheter which has a longitudinal axis and is adapted to be disposed in the vessel and in which the catheter is provided with first, second, third and fourth transducers, the first, second and fourth transducers being positioned on one side of the catheter and the third transducer being positioned on the opposite side of the catheter, the first, second and third transducers comprising a first set of transducers and said first, third and fourth transducers comprising a second set of transducers and instrumentation means connected to the first, second, third and fourth transducers for supplying energy to the transducers and for receiving energy from the transducers, the steps of sensing one set of transducers and then sensing the other set of transducers and ascertaining which of the first and second sets of transducers provides accurate velocity and diameter measurements.

13. A method as in claim 12 together with the step of selecting one of the first and second sets of transducers for providing velocity and diameter measurements.

14. A method as in claim 12 together with the step of periodically sampling the other set of transducers after the first set of transducers has been selected to ascertain whether more accurate information is being provided by the other set of transducers and when such is the case switching to the other set of transducers for providing the velocity and diameter measurements.

15. A method as in claim 12 together with the step of generating an error signal when neither the first nor second set of transducers provides an accurate measurement of the velocity and diameter.

16. A method as in claim 15 together with the step of repositioning the catheter until the error signal disappears.

17. A catheter for making measurements in a vessel defined by a wall carrying a fluid, comprising an elongate flexible tubular member having a plurality of lumens including a balloon inflation lumen extending therethrough and having proximal and distal extremities, an inflatable balloon carried by the distal extremity of the tubular member and having the interior of the balloon in communication with the balloon inflation lumen in the flexible tubular member, the tubular member having at least one preformed bend therein adjacent the distal extremity of the tubular member, a transducer carried by the tubular member in the region of the preformed bend, conductive means connected to the transducer and carried by the tubular member and extending through one of the lumens in the tubular member to the proximal extremity of the tubular member, the tubular member having an opening in the distal extremity distal of the balloon in communication with one of the lumens in the tubular member, and fixed wire means disposed in one of the lumens and extending through said one of the lumens from the proximal extremity into a region which extends beyond the transducer and which is just short of the preformed bend so that the fixed wire provides support for the catheter throughout substantially its entire length except in the region of the predetermined bend and beyond to the distal extremity, the shape of the predetermined bend being such so that it provides stability for the catheter when the catheter is positioned in the pulmonary artery.

18. A catheter as in claim 17 wherein said fixed wire is solid and is formed of stainless steel and has a distal extremity together with a coil spring secured to the distal extremity of the fixed wire.

19. A catheter as in claim 17 wherein said fixed wire is provided with portions having diameters of decreasing size extending in a direction towards the distal extremity o the wire with the exception of a portion in the vicinity of the transducer.

20. A catheter as in claim 17 wherein said fixed wire extends through the balloon inflation lumen which is used for inflating and deflating the inflatable balloon, said fixed wire having a proximal extremity and means for securing the proximal extremity of the wire in the balloon inflation lumen.

21. A catheter as in claim 17 together with a stop clock carried by the elongate flexible tubular member and in communication with the balloon inflation lumen.

22. A method for introducing a catheter for making means in a vessel defined by a wall carrying a fluid by utilizing a catheter having an elongate flexible tubular member having a plurality of lumens extending therethrough and having proximal and distal extremities, an inflatable balloon carried by the distal extremity of the tubular member and having the interior of the balloon in communication with one of the lumens in the flexible tubular member, the tubular member having at least one preformed bend therein adjacent the distal extremity of the tubular member, a transducer carried by the tubular member in the region of the preformed bend, conductive means connected to the transducer and carried by the tubular member and extending through one of the lumens in the tubular member to the proximal extremity of the tubular member, the tubular member having an opening in the distal extremity distal of the balloon in communication with one of the lumens in the tubular member and fixed guide wire means disposed in one of the lumens from the proximal extremity and extending through said one of the lumens to a region which is beyond the transducer but just short of the preformed bend so that the fixed guide wire provides support for the catheter throughout substantially its entire length except in the region of the predetermined bend and beyond towards the distal extremity, the method comprising introducing the catheter into the vessel, inflating the balloon to permit the balloon to flat in the fluid in the vessel and to further advance the catheter in the vessel and manipulating the catheter to cause it to advance into the right atrium, the right ventricle and into the main pulmonary artery and into the right branch of the pulmonary artery.

* * * * *